(12) United States Patent
Lau et al.

(10) Patent No.: US 9,809,833 B2
(45) Date of Patent: Nov. 7, 2017

(54) PATHWAYS TO ADIPATE SEMIALDEHYDE AND OTHER ORGANIC PRODUCTS

(71) Applicant: BioAmber Inc., Plymouth, MN (US)

(72) Inventors: Man Kit Lau, Plymouth, MN (US); Christopher P. Mercogliano, Minneapolis, MN (US)

(73) Assignee: BioAmber Inc., St. Paul, MN (US)

( * ) Notice: Subject to any disclaimer, the term of this patent is extended or adjusted under 35 U.S.C. 154(b) by 40 days.

(21) Appl. No.: 14/418,543

(22) PCT Filed: Sep. 20, 2013

(86) PCT No.: PCT/US2013/060853
§ 371 (c)(1),
(2) Date: Jan. 30, 2015

(87) PCT Pub. No.: WO2014/047407
PCT Pub. Date: Mar. 27, 2014

(65) Prior Publication Data
US 2015/0291987 A1      Oct. 15, 2015

Related U.S. Application Data

(60) Provisional application No. 61/703,361, filed on Sep. 20, 2012.

(51) Int. Cl.
| | | |
|---|---|---|
| *C12P 13/00* | (2006.01) | |
| *C12N 9/04* | (2006.01) | |
| *C12N 9/02* | (2006.01) | |
| *C12N 9/10* | (2006.01) | |
| *C12N 9/16* | (2006.01) | |
| *C12N 9/88* | (2006.01) | |
| *C12P 7/18* | (2006.01) | |
| *C12P 7/40* | (2006.01) | |
| *C12P 7/44* | (2006.01) | |

(52) U.S. Cl.
CPC ............ *C12P 13/001* (2013.01); *C12N 9/001* (2013.01); *C12N 9/0006* (2013.01); *C12N 9/1029* (2013.01); *C12N 9/1096* (2013.01); *C12N 9/13* (2013.01); *C12N 9/16* (2013.01); *C12N 9/88* (2013.01); *C12P 7/18* (2013.01); *C12P 7/40* (2013.01); *C12P 7/44* (2013.01); *C12P 13/005* (2013.01); *C12Y 101/01* (2013.01); *C12Y 103/01* (2013.01); *C12Y 103/08* (2013.01); *C12Y 206/01* (2013.01); *C12Y 208/03* (2013.01); *C12Y 301/02* (2013.01); *C12Y 402/01* (2013.01)

(58) Field of Classification Search
CPC ................ C12P 7/00; C12N 9/24; C12N 9/10
See application file for complete search history.

(56) References Cited

U.S. PATENT DOCUMENTS

2010/0317069 A1*  12/2010  Burk .................. C12N 1/38
                                                  435/121

FOREIGN PATENT DOCUMENTS

| WO | WO2008080124 A2 | 7/2008 |
|---|---|---|
| WO | WO2011137401 A2 | 11/2011 |

* cited by examiner

*Primary Examiner* — Maryam Monshipouri
(74) *Attorney, Agent, or Firm* — Baker & Hostetler LLP

(57) ABSTRACT

Recombinant microorganisms comprising at least one exogenous nucleic acid sequence and capable of producing adipate semialdehyde are provided. Adipate semialdehyde may be produced in a synthesis pathway utilizing a single thiolase reaction. Adipate semialdehyde may also be produced from intermediates consisting of alpha, omega difunctional aliphatic organic molecules. Methods of using recombinant microorganisms to produce 6-aminocaproic acid, adipic acid, hexamethylenediamine and 1.6-hexanediol are also provided.

11 Claims, 3 Drawing Sheets

SEQUENCE LISTING

```
<160> NUMBER OF SEQ ID NOS: 6

<210> SEQ ID NO 1
<211> LENGTH: 1185
<212> TYPE: DNA
<213> ORGANISM: Artificial Sequence
<220> FEATURE:
<223> OTHER INFORMATION: Synthetic Construct

<400> SEQUENCE: 1
atgacccgtg aagtggttgt tgtgtctggc gttcgtaccg caatcggcac gtttggtggc      60
tccctgaaag atgtcgctcc ggctgaactg ggcgcgctgg ttgtgcgtga agcactggct     120
cgcgcgcagg tgtctggcga tgacgttggt catgtcgtgt ttggcaacgt gattcaaacc     180
gaaccgcgtg atatgtatct gggtcgcgtt gcggccgtca acggtggtgt gaccatcaat     240
gccccggcac tgacggttaa tcgtctgtgc ggcagcggtc tgcaagcgat tgtgagcgcg     300
gcgcaaacca tcctgctggg cgatacggac gttgcgattg cggtggcgc  agaaagcatg     360 tctcgcgccc cgtacctggc accggcggca cgttggggtg cacgcatggg cgatgctggt     420
ctggtggaca tgatgctggg cgcgctgcat gatccgtttc atcgtattca catgggtgtc     480
accgctgaaa acgtggcgaa agaatatgat attagccgtg cgcagcaaga cgaagcagct     540
ctggaatcac accgtcgcgc atcggcggcc attaaagcgg gctactttaa ggatcagatc     600
gtgccggttg tctcgaaagg ccgtaagggt gatgttacct tcgatacgga cgagcatgtg     660
cgtcacgacg cgaccattga tgacatgacg aaactgcgcc cggtcttcgt gaaggaaaat     720
```

-continued

```
ggcaccgtta cggctggcaa cgcgagtggt ctgaatgatg cagctgcggc cgtggttatg    780
atggaacgtg ctgaagcgga acgtcgcggt ctgaaaccgc tggcacgtct ggtgtcctat    840
ggccacgcag gtgttgaccc gaaagcaatg gcattggtc cggtgccggc caccaagatc    900
gcactggaac gtgctggtct gcaagtttct gatctggacg tcattgaagc caacgaagca    960
tttgcagctc aggcctgcgc agtcacgaaa gcgctgggtc tggacccggc aaaggttaac   1020
ccgaatggca gtggtatttc cctgggtcat ccgatcggcg ctaccggtgc gctgatcacg   1080
gttaaagcac tgcacgaact gaatcgtgtc cagggtcgtt acgccctggt gaccatgtgt   1140
attggtggcg gtcaaggtat tgcggccatc ttcgaacgca tctaa                   1185
```

<210> SEQ ID NO 2
<211> LENGTH: 394
<212> TYPE: PRT
<213> ORGANISM: Cupriavidus necator

<400> SEQUENCE: 2

```
Met Thr Arg Glu Val Val Val Ser Gly Val Arg Thr Ala Ile Gly
 1               5                  10                  15

Thr Phe Gly Gly Ser Leu Lys Asp Val Ala Pro Ala Glu Leu Gly Ala
                20                  25                  30

Leu Val Val Arg Glu Ala Leu Ala Arg Ala Gln Val Ser Gly Asp Asp
            35                  40                  45

Val Gly His Val Val Phe Gly Asn Val Ile Gln Thr Glu Pro Arg Asp
        50                  55                  60

Met Tyr Leu Gly Arg Val Ala Ala Val Asn Gly Gly Val Thr Ile Asn
 65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
           100                 105                 110

Ile Gly Gly Gly Ala Glu Ser Met Ser Arg Ala Pro Tyr Leu Ala Pro
       115                 120                 125

Ala Ala Arg Trp Gly Ala Arg Met Gly Asp Ala Gly Leu Val Asp Met
   130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
           180                 185                 190

Ala Gly Tyr Phe Lys Asp Gln Ile Val Pro Val Val Ser Lys Gly Arg
       195                 200                 205

Lys Gly Asp Val Thr Phe Asp Thr Asp Glu His Val Arg His Asp Ala
   210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255

Ala Val Val Met Met Glu Arg Ala Glu Ala Arg Arg Gly Leu Lys
           260                 265                 270

Pro Leu Ala Arg Leu Val Ser Tyr Gly His Ala Gly Val Asp Pro Lys
       275                 280                 285

Ala Met Gly Ile Gly Pro Val Pro Ala Thr Lys Ile Ala Leu Glu Arg
```

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
            325                 330                 335

Ala Lys Val Asn Pro Asn Gly Ser Gly Ile Ser Leu Gly His Pro Ile
        340                 345                 350

Gly Ala Thr Gly Ala Leu Ile Thr Val Lys Ala Leu His Glu Leu Asn
    355                 360                 365

Arg Val Gln Gly Arg Tyr Ala Leu Val Thr Met Cys Ile Gly Gly Gly
370                 375                 380

Gln Gly Ile Ala Ala Ile Phe Glu Arg Ile
385                 390

<210> SEQ ID NO 3
<211> LENGTH: 1182
<212> TYPE: DNA
<213> ORGANISM: Artificial Sequence
<220> FEATURE:
<223> OTHER INFORMATION: Synthetic Construct

<400> SEQUENCE: 3

```
atgacggacg ttgttattgt gtcggcggct cgcacggctg tcggcaaatt cggtggctct    60
ctggcaaaaa tcccggctcc ggaactgggt gcagtggtta ttaaagcagc actggaacgt   120
gcaggtgtga agccggaaca agtcagcgaa gtgatcatgg gtcaagttct gaccgcaggt   180
tctggtcaga cccggctcg tcaagcagct attaaagcag gcctgccggc tatggttccg   240
gcgatgacga tcaacaaagt ctgcggtagc ggtctgaagg cagtgatgct ggcagcaaat   300
gctattatgg cggtgatgc cgaaatcgtc gtggccggcg tcaggaaaaa tatgtcagca   360
gctccgcatg ttctgccggg ttcgcgtgac ggctttcgca tgggtgatgc gaaactggtg   420
gataccatga ttgtggatgg cctgtgggac gtctataacc agtaccacat gggtattacc   480
gccgaaaatg ttgcaaaaga atatggcatc acccgtgaag cgcaggatga atttgccgtg   540
ggctctcaga acaaggcgga agcggcccaa aaagccggca agttcgacga agaaattgtt   600
ccggtcctga tcccgcagcg taaaggcgat ccggttgcct taagaccga cgaatttgtc   660
cgccaaggcg caacgctgga tagcatgtct ggtctgaaac cggcttttga caaggcaggc   720
accgtgacgg cagctaacgc gagtggcctg aatgatggtg cggccgcagt tgtcgtgatg   780
tccgctgcga aagcaaagga actgggtctg accccgctgg caacgattaa atcatacgct   840
aacgcgggtg ttgatccgaa ggtcatgggt atgggtccgg tgccggcaag taaacgtgca   900
ctgtcccgcg ctgaatggac cccgcaggat ctggacctga tggaaatcaa tgaagcgttc   960
gccgcacaag ccctggcagt tcatcagcaa atgggctggg ataccctcaaa agtgaacgtt  1020
aatggcggtg ctattgcgat cggtcatccg attggtgcct cgggctgccg tatcctggtg  1080
acgctgctgc acgaaatgaa acgtcgcgat gcaaaaaagg gtctggcttc cctgtgtatt  1140
ggcggtggca tgggtgtggc actggcagtt gaacgcaaat aa                     1182
```

<210> SEQ ID NO 4
<211> LENGTH: 393
<212> TYPE: PRT
<213> ORGANISM: Ralstonia sp., strain EMBL EON20543.1

<400> SEQUENCE: 4

Met Thr Asp Val Val Ile Val Ser Ala Ala Arg Thr Ala Val Gly Lys

```
1               5                    10                    15
    Phe Gly Gly Ser Leu Ala Lys Ile Pro Ala Pro Glu Leu Gly Ala Val
                    20                   25                   30

Val Ile Lys Ala Ala Leu Glu Arg Ala Gly Val Lys Pro Glu Gln Val
                    35                   40                   45

Ser Glu Val Ile Met Gly Gln Val Leu Thr Ala Gly Ser Gly Gln Asn
                    50                   55                   60

Pro Ala Arg Gln Ala Ala Ile Lys Ala Gly Leu Pro Ala Met Val Pro
    65                   70                   75                   80

Ala Met Thr Ile Asn Lys Val Cys Gly Ser Gly Leu Lys Ala Val Met
                    85                   90                   95

Leu Ala Ala Asn Ala Ile Met Ala Gly Asp Ala Glu Ile Val Val Ala
                    100                  105                  110

Gly Gly Gln Glu Asn Met Ser Ala Pro His Val Leu Pro Gly Ser
                    115                  120                  125

Arg Asp Gly Phe Arg Met Gly Asp Ala Lys Leu Val Asp Thr Met Ile
                    130                  135                  140

Val Asp Gly Leu Trp Asp Val Tyr Asn Gln Tyr His Met Gly Ile Thr
    145                  150                  155                  160

Ala Glu Asn Val Ala Lys Glu Tyr Gly Ile Thr Arg Glu Ala Gln Asp
                    165                  170                  175

Glu Phe Ala Val Gly Ser Gln Asn Lys Ala Glu Ala Ala Gln Lys Ala
                    180                  185                  190

Gly Lys Phe Asp Glu Glu Ile Val Pro Val Leu Ile Pro Gln Arg Lys
                    195                  200                  205

Gly Asp Pro Val Ala Phe Lys Thr Asp Glu Phe Val Arg Gln Gly Ala
                    210                  215                  220

Thr Leu Asp Ser Met Ser Gly Leu Lys Pro Ala Phe Asp Lys Ala Gly
    225                  230                  235                  240

Thr Val Thr Ala Ala Asn Ala Ser Gly Leu Asn Asp Gly Ala Ala Ala
                    245                  250                  255

Val Val Val Met Ser Ala Ala Lys Ala Lys Glu Leu Gly Leu Thr Pro
                    260                  265                  270

Leu Ala Thr Ile Lys Ser Tyr Ala Asn Ala Gly Val Asp Pro Lys Val
                    275                  280                  285

Met Gly Met Gly Pro Val Pro Ala Ser Lys Arg Ala Leu Ser Arg Ala
                    290                  295                  300

Glu Trp Thr Pro Gln Asp Leu Asp Leu Met Glu Ile Asn Glu Ala Phe
    305                  310                  315                  320

Ala Ala Gln Ala Leu Ala Val His Gln Gln Met Gly Trp Asp Thr Ser
                    325                  330                  335

Lys Val Asn Val Asn Gly Gly Ala Ile Ala Ile Gly His Pro Ile Gly
                    340                  345                  350

Ala Ser Gly Cys Arg Ile Leu Val Thr Leu Leu His Glu Met Lys Arg
                    355                  360                  365

Arg Asp Ala Lys Lys Gly Leu Ala Ser Leu Cys Ile Gly Gly Gly Met
                    370                  375                  380

Gly Val Ala Leu Ala Val Glu Arg Lys
    385                  390

<210> SEQ ID NO 5
<211> LENGTH: 1179
<212> TYPE: DNA
<213> ORGANISM: Artificial Sequence
```

<220> FEATURE:
<223> OTHER INFORMATION: Synthetic Construct

<400> SEQUENCE: 5

```
atgaaagaag tcgttatcgc tagtgctgtt cgcaccgcca ttggttccta cggcaaatcc    60
ctgaaagatg tcccggcagt tgacctgggt gcgaccgcca ttaaagaagc agtcaaaaag   120
gctggcatca aaccggaaga tgtcaacgaa gtgattctgg taacgtgct gcaagcaggt    180
ctgggtcaaa acccggcacg tcaggcctca tttaaagccg gcctgccggt ggaaattccg   240
gcaatgacca tcaataaagt gtgcggtagt ggtctgcgta cggtttccct ggcagcacaa   300
attatcaaag caggtgatgc tgacgttatt atcgcaggcg gtatgaaaaa catgagccgt   360
gcgccgtatc tggcgaacaa tgcccgttgg ggttaccgca tgggcaacgc caaatttgtg   420
gatgaaatga ttaccgatgg tctgtgggac gcattcaatg attatcacat gggcattacg   480
gcggaaaaca tcgccgaacg ttggaatatc agccgcgaag aacaagacga atttgcactg   540
gctagccaga aaaggcaga agaagctatt aaatctggcc agttcaagga tgaaattgtt   600
ccggtggtta tcaaaggtcg taagggcgaa accgtcgtgg atacggacga cacccgcgc    660
tttggttcta ccatcgaagg cctggcaaaa ctgaagccgg ctttcaaaaa ggacggcacc   720
gtgacggcgg gtaacgccag tggcctgaat gattgtgcag ctgttctggt cattatgtcc   780
gcagaaaaag ctaaggaact gggtgtgaaa ccgctggcga agatcgttag ctacggttct   840
gcgggcgttg atccggccat tatgggttat ggcccgttct acgcgaccaa agcggccatc   900
gaaaaggccg gctggacggt tgatgaactg gacctgattg aatcaaacga agcgtttgca   960
gctcagtcgc tggccgtcgc caaagacctg aagttcgata tgaacaaggt gaacgttaac  1020
ggcggtgcaa ttgctctggg tcatccgatc ggtgcatcag cgcccgtat tctggttacc   1080
ctggtccacg cgatgcaaaa acgcgatgca aaaaagggtc tggctaccct gtgcattggc  1140
ggtggccagg cacggcaat cctgctggaa aatgttaa                          1179
```

<210> SEQ ID NO 6
<211> LENGTH: 392
<212> TYPE: PRT
<213> ORGANISM: Clostridium acetobutylicum

<400> SEQUENCE: 6

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140
```

```
Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
                340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390
```

US 9,809,833 B2

PATHWAYS TO ADIPATE SEMIALDEHYDE AND OTHER ORGANIC PRODUCTS

FIELD

This disclosure relates to recombinant microorganisms and methods of producing organic molecules, such as adipate semialdehyde, adipic acid, 6-hydroxycaproic acid, aminocaproic acid, hexamethylenediamine, and 1,6 hexane diol.

BACKGROUND

Crude oil is the number one starting material for the synthesis of key chemicals and polymers. As oil becomes increasingly scarce and expensive, biological processing of renewable raw materials in the production of chemicals using live microorganisms or their purified enzymes becomes increasingly interesting. Biological processing, in particular, fermentations have been used for centuries to make beverages. Over the last 50 years, microorganisms have been used commercially to make compounds such as antibiotics, vitamins, and amino acids. However, the use of microorganisms for making industrial chemicals has been much less widespread. It has been realized that microorganisms are able to provide biosynthetic routes to certain compounds. However, such biosynthetic routes can be economically unreasonable depending upon their efficiency.

SUMMARY

The engineered biosynthetic pathways, such as those described herein for making adipate semialdehyde, adipic acid, 6-hydroxycaproic acid, aminocaproic acid, hexamethylenediamine, and 1,6 hexane diol (hereinafter "Products") are desirable and can provide energetically favorable alternatives to prior published pathways leading to similar Products. The pathways described herein can also avoid the use of a metabolically problematic P450 step, utilize intermediates with favorable aqueous solubility and/or can be cultured under low oxygen condition. The engineered biosynthetic pathways described herein also alleviate the need for comparable products from the petrochemical industry. One of ordinary skill in the art will appreciate that the selection of a particular host, an engineered biosynthetic pathway and enzymes within that selected engineered biosynthetic pathway will depend upon many factors, including for example, geographic location of production, the variety of feedstock available, and the prevailing regularity environment. Hence, while technical factors such as yield of product based on carbon input can be important, they are not solely determinative for allowing industries to shift away from petrochemical derived sources of products to renewable sources, such as described herein.

Described herein are useful compounds such as adipate semialdehyde, adipic acid, 6-hydroxycaproic acid, aminocaproic acid, hexamethylenediamine, and 1,6 hexane diol. These compounds are useful for the production of polymers from carbohydrate feedstocks. These compounds can be made at least partially from recombinant microorganisms that are also described herein. Some of the recombinant microorganisms described herein are engineered to express one or more enzymes that catalyze a substrate to product conversion comprising acetyl-CoA and 4-hydroxybutyryl-CoA to 6-hydroxy-3-oxo-hexanoyl-CoA; malonyl-CoA and 4-hydroxybutyryl-CoA to 6-hydroxy-3-oxo-hexanoyl-CoA, and maloyl-ACP and 4-hydroxybutyryl-CoA to 6-hydroxy-3-oxo-hexanoyl-CoA (FIG. 2). Microorganisms described herein can additionally express one or more enzymes that catalyze substrate to product conversions selected from 6-hydroxy-3-oxo-hexanoyl-CoA to 3,6-dihydroxyhexanoyl-CoA, 3,6-dihydroxyhexanoyl-CoA to 6-hydroxy-2-hexenoyl-CoA, 6-hydroxy-2-hexenoyl-CoA to 6-hydroxyhexanoyl-CoA, 6-hydroxyhexanoyl-CoA to 6-hydroxycaproic acid, 6-hydroxycaproic acid to adipate semialdehyde, adipate semialdehyde to adipic acid, and adipate semialdehyde to 6-aminocaproic acid, and methods of using such a recombinant microorganism to make Products. Enzymes that can be used for such conversions include those shown in Tables 1-9, as well as those shown in the Examples, below.

In some of the pathways described herein the microorganism is additionally engineered to express one or more enzymes that divert succinate to 4-hydroxybutyryl-CoA (see, FIG. 1). Reactant to product conversions in such pathways include succinate to succinyl-CoA, succinate to succinate semialdehyde, succinyl-CoA to succinate semialdehyde, succinate semialdehyde to 4-hydroxybutyric acid, to 4-hydroxybutyric acid to 4-hydroxybutyryl phosphate, 4-hydroxybutyric acid to 4-hydroxybutyryl-CoA, and 4-hydroxybutyryl phosphate to 4-hydroxybutyryl-CoA. Enzymes that can be used for such conversions include succinyl-CoA synthase, succinyl semialdehyde dehydrogenase, succinyl-CoA reductase, 4-hydroxybutyrate dehydrogenase, 4-hydroxyputyrate kinase, 4-hydroxyputyryl-CoA synthetase and phosphor-transferase, respectively (see, FIG. 1, and US2013/0029381 which is herein incorporated by reference).

In some of the pathways described herein the intermediates in the pathway are selected for their aqueous solubility. Pathways containing intermediates that have higher aqueous solubility can be beneficial for overall efficiency. For example, the intermediates can be alpha, omega difunctional aliphatic organic molecules (as further described below) and these intermediates can have an aqueous solubility greater than 20 mg/mL, 22 mg/mL, 25 mg/mL or even greater than 50 mg/mL.

Methods are also provided for making products via culturing the recombinant microorganisms and separating the products from the fermentation broth. Such methods include methods of making adipate semialdehyde, adipic acid, 6-hydroxycaproic acid, aminocaproic acid, hexamethylenediamine, and 1,6 hexane diol, and combinations thereof.

The recombinant microorganisms used in the methods described herein can express one or more exogenous nucleic acid sequences that encode one or more polypeptides having activities selected from Tables 1-9. The recombinant microorganisms provided herein can in addition to expressing one or more of the enzymes provided in Tables 1-9, express one or more polypeptides described in US2013/0029381 (describing enzymes useful for 4-hydroxybutyryl-CoA production) and/or one or more polypeptides described in EP2220232 (describing pathways for succinate production), both of which are incorporated herein by reference.

As previously described, the recombinant microorganisms described herein can be used to produce adipate semialdehyde, adipic acid, 6-hydroxycaproic acid, aminocaproic acid, hexamethylenediamine, and 1,6 hexanediol. These products are useful in a variety of polymers, for example polyesters and polyurethanes. For example, polyamides are high performance semi-crystalline engineered thermoplastics which are known for their tough, high modulus and tensile strength. Compounds based on this thermoplastic are often compounded with additional reinforcing additives such as pigments, clay, talc, silica nanoparticles and carbon black can be converted into molded plastic articles useful in rigid engineering structures such as automotive interiors, structural high temperature applications such as machine components (gears, fan blades, pumps and alternator housings or so called "under hood automotive applications"). In addition, Nylon 6 and its compounds can be injection molded or extruded into sheets, films and fibers. Moreover, polyamides can be coextruded with elastomers such as natural rubber, epichlorhydrin rubber, acrylic-nitrile rubber and the like to make veneer hoses useful in low permeation solvent resistant fuel line hose and tubing applications.

Moreover, if the lactam or 6-ACA is formulated with an excess of a diamine compound such ethylene diamine or similar diamines, the stoichiometric overcharge of the diamine can produce amine end capped polyamides useful as reactive diluents in polyurethane, polyureas, epoxy and polyester, polyamide and polyimide thermosetting materials.

Thus the use of a bio based materials derived from 6-ACA increases the renewable content and over all reduces the carbon footprint of these types of engineering plastic structures.

DETAILED DESCRIPTION

Described herein are recombinant microorganisms for efficiently producing adipate semialdehyde, adipic acid, 6-hydroxycaproic acid, aminocaproic acid, hexamethylenediamine, 1,6 hexanediol and combinations thereof. These products are produced by any microorganism capable of making succinic acid and salts thereof. One of ordinary skill in the art will appreciate that microorganisms can ferment various carbohydrate feedstocks to produce succinate and that such microorganisms can be either recombinant microorganisms or microorganisms that naturally produce succinic acid and salts thereof. Methods of increasing the production of succinic acid and salts thereof are known in the art and can be accomplished through fermentation techniques, genetic engineering and combinations thereof. Examples of methods of increasing succinic acid and salts thereof from microorganisms are described in the following publication EP2220232.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The terms "comprise" and "comprising" are used in the inclusive, open sense, meaning that additional elements may be included.

The terms "host cell" and "recombinant microorganism" are used to describe the cell into which the altered nucleic acid sequence has been introduced. The altered nucleic acid sequence can be created by insertions of new nucleic acid sequences, deletions of base pairs, and combinations thereof.

The term "including" is used to mean "including but not limited to".

Figure 1:
FIG. 1 shows the chemical structures of reactants and products in an exemplary pathway that can be used to obtain 4-hydroxybutyryl-CoA from succinate. Any succinate producing microorganism can be used to express the various pathways described herein, including pathways for example described in EP2220232 for the overproduction of succinate.
Figure 2:
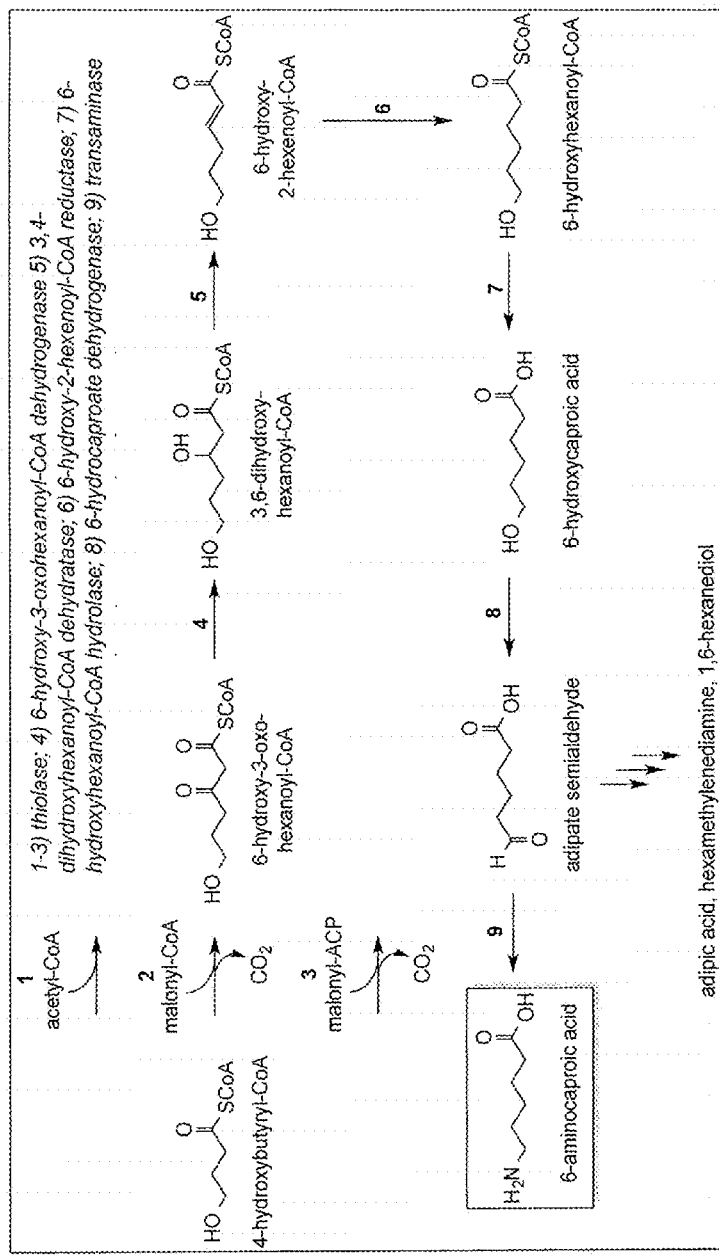
FIG. 2 shows the chemical structures of reactants and products in an exemplary pathway that can be used to obtain adipate semialdehyde, adipic acid, 6-hydroxycaproic acid, hexamethylenediamine, 1,6-hexanediol, and aminocaproic acid from 4-hydroxybutyryl-CoA. The numbers adjacent to the arrows correspond to the reactions described in the text and the accompanying Tables. The enzyme classification number (E.C.) associated with enzymes that can be used for the indicated reaction are provided in the corresponding table.

The term "product" refers to intermediates shown in FIGS. 1 and 2, as well as adipate semialdehyde, adipic acid, 6-hydroxycaproic acid, aminocaproic acid, hexamethylenediamine, and 1,6 hexane diol.

The term "alcohol" refers, for example, to an alkyl moiety in which one or more of the hydrogen atoms has been replaced by an —OH group. The term "primary alcohol" refers, for example to alcohols in which the —OH group is bonded to a terminal or chain-ending carbon atom, such as in 1-hexanol and the like. The term "secondary alcohol" refers, for example to alcohols in which the —OH group is bonded to a carbon atom that is bonded to one hydrogen atom and to two other carbon atoms, such as in 2-hexanol and the like. The term "tertiary alcohol" refers, for example to alcohols in which the —OH group is bonded to a carbon atom that is bonded to three other carbon atoms.

The term "amine" refers, for example, to an alkyl moiety in which one or more of the hydrogen atoms has been replaced by an —NH2 group.

The term "carbonyl compound" refers, for example, to an organic compound containing a carbonyl group, C=O, such as, for example, aldehydes, which have the general formula RCOH; ketones, which have the general formula RCOR'; carboxylic acids, which have the general formula RCOOH; and esters, which have the general formula RCOOR'.

The term "codon optimization" or "codon-optimized" refers to modifying the codon content of a nucleic acid sequence without modifying the sequence of the polypeptide encoded by the nucleic acid to enhance expression in a particular host cell. In certain embodiments, the term is meant to encompass modifying the codon content of a nucleic acid sequence as a means to control the level of expression of a polypeptide (e.g., to either increase or decrease the level of expression).

The term "alpha, omega difunctional aliphatic organic molecule" refers to molecules containing a carbon chain containing at least two carbon atoms bound to each other, wherein the terminal carbon atoms in the chain are the alpha and omega carbons. The alpha and omega carbon atoms contain chemical bonds that are not 3 hydrogen bonds. For example, one terminal carbon atom can contain a bond to an oxygen atom and the opposite terminal carbon atom can contain a bond to a nitrogen atom. Stated another way, the alpha, omega difunctional ends of the alpha, omega difunctional aliphatic organic molecule can be C=C, —OH, =O, —N, or any of the functional groups shown on the terminal ends of the carbon chains shown in FIGS. 1 and 2. The carbon atoms internal to the alpha, omega carbon atoms can also be bound to any other atom known to one or ordinary skill in the art, for example —OH, C═C, ═O, —N and the like.

The term "metabolic pathway" refers to a series of two or more enzymatic reactions in which the product of one enzymatic reaction becomes the substrate for the next enzymatic reaction. At each step of a metabolic pathway, intermediate compounds are formed and utilized as substrates for a subsequent step. These compounds may be called "metabolic intermediates." The products of each step are also called "metabolites."

The terms "nucleotide sequence", "nucleic acid sequence" and "genetic construct" are used interchangeably and mean a polymer of RNA or DNA, single- or double-stranded, optionally containing synthetic, non-natural or altered nucleotide bases. A nucleotide sequence may comprise one or more segments of cDNA, genomic DNA, synthetic DNA, or RNA. In a preferred embodiment, the nucleotide sequence is codon-optimized to reflect the typical codon usage of the host cell without altering the polypeptide encoded by the nucleotide sequence.

The term "organic molecule" refers, for example, to any molecule that is made up predominantly of carbon and hydrogen, such as, for example, alkanes. Organic molecules of interest, include intermediates such as those shown in FIG. 2, for example, 4-hydroxybutyryl-CoA, 6-hydroxy-3-oxo-hexanoyl-CoA, 3,6-dihydroxy-hexanoyl-CoA, 6-hydroxy-2-hexenoyl-CoA, 6-hydroxyhexanoyl-CoA, 6-hydroxycaproic acid, adipate semialdehyde, 6-aminocaproic acid, adipic acid, hexamethylenediamine, and 1,6-hexanediol.

The terms "polypeptide," "protein" and "peptide," which are used interchangeably herein, refer to a polymer of amino acids, including, for example, gene products, naturally-occurring proteins, homologs, orthologs, paralogs, fragments, and other equivalents, variants and analogs of the forgoing. The term "polypeptide having enzymatic activity" refers to any polypeptide that catalyzes a chemical reaction of other substances without itself being destroyed or altered upon completion of the reaction. Typically, a polypeptide having enzymatic activity catalyzes the formation of one or more products from one or more substrates. In some aspects of the invention, the catalytic promiscuity properties of some enzymes may be combined with protein engineering and may be exploited in novel metabolic pathways and biosynthesis applications. In some embodiments, existing enzymes are modified for use in organic biosynthesis.

The term "recombinant" or "genetically modified" as used herein refers to a host cell that contains an altered nucleic acid sequence that is not found in the wild type host cell. Recombinant host cells can have new metabolic capabilities or new metabolic pathways. As used herein the term genetically modified, with reference to microorganisms, refers to microorganisms having at least one genetic alteration not normally found in the wild type strain of the reference species. In some embodiments, genetically engineered microorganisms are engineered to express or overexpress at least one particular enzyme at critical points in a metabolic pathway, and/or to block the synthesis of other enzymes, to overcome or circumvent metabolic bottlenecks.

The term "sequence identity" is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are publicly available in the form of computer programs. Preferred computer program methods to determine identity and similarity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix. The sequence of the enzymes disclosed herein can be altered while still maintaining enzymatic activity. For example sequences that share 40, 50, 60, 70, 80, 90 or 95% sequence identity with the sequences shown in SEQ ID NOS. 1-6 and/or the sequences in Tables 1-9, can be used as long as they continue to maintain the desired enzymatic functions.

A Making Recombinant Microorganisms

As described in US publication number 2013/0029381, Example XIII, and more specifically paragraph 0455, 4-hydroxybutyryl-CoA can be produced in recombinant microorganisms. Therefore, the pathways described in US publication number 2013/0029381 can be combined with those pathways shown in FIG. 2, to produce Products.

The Products described herein can be made using recombinant microorganisms. Genetically engineered microorganisms can include exogenous polypeptides, and polynucleotides encoding such polypeptides. Such polypeptides can have enzymatic activity or an improved activity for a natural or unnatural substrate or have broad substrate specificity (e.g., catalytic promiscuity such as substrate promiscuity). In some instances, the enzymes involved in the production of the products are selected from acetyltransferase thiolase (E.C. 2.3.1._), CoA synthase-decarboxylase thiolase (E.C. 2.3.1._), an ACP synthase decarboxylase thiolase (E.C. 2.3.1._), a 3-oxo-CoA dehydrogenase (1.1.1._), enolyl-CoA dehydratase (E.C. 4.2.1._), acrylyl-CoA reductase (E.C. 1.3.1._), acyl-CoA dehydrogenase (E.C. 1.3.8._), CoA transferase (E.C. 2.8.3._), thioesterase (E.C. 3.1.2._), dehydrogenase (E.C. 1.1.1._), and transaminase (E.C. 2.6.1._), and an alcohol dehydrogenase (E.C. 1.1.1._). In some embodiments, the reaction mechanism of the enzyme chosen from the relevant tables (see, Tables 1-9) may be altered to catalyze new reactions, to change, expand or improve substrate specificity. One should appreciate that if the enzyme structure (e.g. crystal structure) is known, enzymes properties may be modified by rational redesign (see US patent application US20060160138, US20080064610 and US20080287320). Modification or improvement in enzyme properties may arise from the introduction of modifications into a polypeptide chain that may, in effect, perturb the structure-function of the enzyme and/or alter its interaction with another molecule (e.g., association with a natural substrate versus an unnatural substrate). It is well known in the art that certain regions of a protein may be critical for enzyme activity, for example amino acids involved in catalysis and substrate binding domains, such that small perturbations to these regions will have significant effects on enzyme function. Some amino acid residues may be at important positions for maintaining the secondary or tertiary structure of the enzyme, and thus also produce noticeable changes in enzyme properties when modified. In some embodiments, the potential pathway components are variants of any of the foregoing. Such variants may be produced by random mutagenesis or may be produced by rational design for production of an enzymatic activity having, for example, an altered substrate specificity, increased enzymatic activity, greater stability, etc. Thus, in some embodiments, the number of modifications to an enzyme initially chosen from Tables 1-9 (hereinafter a parent enzyme) that produces a variant enzyme having the desired property may comprise one or more amino acids, 2 or more amino acids, 5 or more amino acids, 10 or more amino acids, or 20 or more amino acids, up to 10% of the total number of amino acids, up to 20% of the total number of amino acids, up to 30% of the total number of amino acids, up to 40% of the total number of amino acids making up the reference enzyme, or up to 50% of the total number of amino acids making up the reference enzyme.

Those skilled in the art will understand that the engineered pathways exemplified herein are described in relation to, but are not limited to, species specific genes and proteins and that the invention encompasses homologs and orthologs of such gene and protein sequences. Homolog and ortholog sequences possess a relatively high degree of sequence identity/similarity when aligned using methods known in the art. Such homologs or orthologs can suitably be obtained by means of any appropriate cloning strategy known to one skilled in the art. In some embodiments, useful polypeptide sequences have at least 30%, at least 45%, at least 60%, at least 75%, at least 85%, or at least 95% identity to the amino acid sequence of the reference enzyme of interest.

Aspects of the invention provide methods for designing and making engineered metabolic pathways. In some aspects of the invention, alternative pathways for making a product of interest from one or more available and sustainable substrates may be made in one or more host cells or microorganisms of interest. One of ordinary skill in the art will appreciate that the engineered pathway for making products may involve multiple enzymes and therefore the flux through the pathway may not be optimum for the production of the product of interest. Consequently, in some aspects of the invention, the carbon flux is optimally balanced by modulating the activity level of the pathway enzymes relative to one another. Examples of such modulation are provided throughout the application. As used herein the term "carbon flux" refers to the number of feedstock molecules (e.g. glucose) which proceed down the engineered pathway relative to competitive paths.

Host cells can be eukaryotic, prokaryotic, derived from a multicellular organism (e.g. cell line) cultured as a unicellular entity. Exemplary, host cells include bacterial, yeast, insect or mammalian. Bacterial host cells can be selected from *Escherichia coli, Bacillus subtilis, Mycobacterium* spp., *M. tuberculosis*, or other suitable bacterial cells. Archaea host cells can be *Methanococcus Jannaschii* or *Methanococcus Maripaludis* or other suitable archaic cells. Yeast cells can be *Saccharomyces* species such as *S. cerevisiae, S. pombe, Picchia* species, *Candida* species such as *C. albicans*, or other suitable yeast species.

In some embodiments, a host cell may be selected for subsequent genetic modification because of its particular metabolic properties, its ability to utilize particular carbon sources, and its ability to live under certain conditions, such as for example at an acidic pH or at a high temperature. For example, if a selection or screen is related to a particular metabolic pathway, it may be helpful to use a host cell that has a related pathway. Such a host cell may have certain physiological adaptations that allow it to process or import or export one or more intermediates or products of the pathway. However, in other embodiments, a host cell that expresses no enzymes associated with a particular pathway of interest may be selected in order to be able to identify all of the components required for that pathway using appropriate sets of genetic elements and not relying on the host cell to provide one or more missing steps.

According to aspects of the invention, aerobic or anaerobic microorganisms are metabolically engineered. As used herein, an anaerobic organism is any organism that does not require oxygen for growth (i.e. anaerobic conditions), such as certain bacterial cells. Advantageously, the bacterial cell can be an *E. coli, C. glutamicum, B. flavum* or *B. lactofermentum* Cell; these strains are currently being employed industrially to make amino compounds using bacterial fermentation processes. For example, *C. glutamicum* has been used extensively for amino acid production (e.g. L-glutamate, L-lysine, see Eggleging L et al., 2005, Handbook for *Corynebacterium glutamicum*. Boca Raton, USA: CRC Press).

The metabolically engineered cell of the invention is made by transforming a host cell with at least one nucleotide sequence encoding enzymes involved in the engineered metabolic pathways. Accordingly, aspects of the invention include nucleic acid sequences encoding the enzymes involved in the engineered metabolic pathways. In some embodiments, a metabolically engineered cell may express one or more polypeptides having an enzymatic activity necessary to perform the steps shown in FIG. 2. For example, a particular cell comprises one, two, three, four, five or more than five nucleic acid sequences with each one encoding a polypeptide necessary to perform the conversion of a reactant into a product. In some instances the product in turn becomes the reactant for a subsequent reaction in the pathway, see FIG. 2. Alternatively, a single nucleic acid molecule can encode one, or more than one, polypeptide. For example, a single nucleic acid molecule can contain nucleic acid sequences that encode two, three, four or even five different polypeptides. Nucleic acid sequences useful for the invention described herein may be obtained from a variety of sources such as, for example, amplification of cDNA sequence, DNA libraries, de novo synthesis, excision of genomic segments, etc. The sequences obtained from such sources may then be modified using standard molecular biology and/or recombinant DNA technology to produce nucleic acid sequences having the desired modifications. Exemplary methods for modification of nucleic acid sequences include for example, site directed mutagenesis, PCR mutagenesis, deletion, insertion, or substitution, or swapping portions of the sequence using restriction enzymes, optionally in combination with ligation, homologous recombination, site specific recombination or various combination thereof. In other embodiments, the nucleic acid sequence may be a synthetic nucleic acid sequence. Synthetic polynucleotide sequences may be produced using a variety of methods described in U.S. Pat. No. 7,323,320, and in copending application having Ser. No. 11/804,996 and in U.S. Patent Publication Nos. 2006/0160138, 2007/0269870, 2008/0064610, and 2008/0287320.

Methods of transformation for bacteria, plant, yeast and animal cells are well known in the art. Common bacterial transformation methods include electroporation and chemical treatment.

In some embodiments, a culture of a genetically modified host cell is fermented such that it produces when cultured in vitro in a suitable medium, the product of interest or an intermediate at a level of at least 0.1 g/l, at least 1 g/l, at least 10 g/l, at least 50 g/l, at least 100 g/l or at least 150 g/l. One of ordinary skill in the art will appreciate that intermediates can be produced, separated and used in subsequent chemical or enzymatic reactions to produce additional products. In these instances the intermediate is also referred to as a product. One should appreciate that the level of the metabolite of interest or its metabolic intermediates produced by a genetically modified host cell can be controlled in various ways. In some embodiments, the level of expression is controlled by the number of copies of the nucleic acid sequences encoding one or more enzymes involved in the engineered pathway that are contained in the host cell (e.g. high copy expression vector versus medium or low copy expression vectors, copies genomically introduced). Preferably, the nucleic acid sequences are introduced into the cell using a vector. Low copy expression vectors generally provide fewer than 20 vector copies per cell (e.g. from 1 to about 5, from 5 to about 10, from 10 to about 15, from 15 to about 20 copies of the expression vector per cell). Suitable low copy expression vectors for prokaryotic cells (e.g. *E. Coli*) include, but are not limited to pAYC184, pBeloBac11, pBR332, pBAD33, pBBR1MCS and its derivatives, pSC101, SuperCos (cosmid) and pWE15 (cosmid). Medium copy number expression vectors generally provide from about 20 to about 50 expression vectors copies per cell or form about 20 to 80 expression vectors copies per cell. Suitable medium copy expression vectors for prokaryotic cells (e.g. *E. Coli*) include, but are not limited to, pTrc99A, pBAD24 and vectors containing a ColE1 origin of replication and its derivatives. High copy number expression vectors generally provide from about 80 to about 200 or more expression vector copies per cell. Suitable high copy expression vectors for prokaryotic cells (e.g. *E. Coli*) include, but are not limited to, pUC, PCV1, pBluescript, pGEM and pTZ vectors.

Aspects of the invention provide expression cassettes comprising a nucleic acid or a subsequence thereof encoding a polypeptide involved in the engineered pathway. In some embodiments, the expression cassette can comprise the nucleic acid operably linked to control sequences, such as a transcriptional elements (e.g. promoter) and to a terminator. As used herein, the term "cassette" refers to a nucleotide sequence capable of expressing a particular gene if the gene is inserted so as to be operably linked to one or more regulatory sequences present in the nucleotide sequence. Thus, for example, the expression cassette may comprise a heterologous gene which is desired to be expressed in the host cell. In some embodiments, one or more expression cassettes may be introduced into a vector by known recombinant techniques. A promoter is a sequence of nucleotides that initiates and controls the transcription of a desired nucleic acid sequence by an RNA polymerase enzyme. In some embodiments, the promoter may be inducible. In other embodiments, promoters may be constitutive. Non limiting examples of suitable promoters for the use in prokaryotic host cells include a bacteriophage T7 RNA polymerase promoter, a trp promoter, a lac operon promoter and the like. Non limiting examples of suitable strong promoters for the use in prokaryotic cells include lacUV5 promoter, T5, T7, Trc, Tac and the like. Non limiting examples of suitable promoters for use in eukaryotic cells include a CMV immediate early promoter, a SV40 early or late promoter, a HSV thymidine kinase promoter and the like. Termination control regions may also be derived from various genes native to the preferred host.

In some embodiments, a first enzyme of the engineered pathway may be under the control of a first promoter and the second enzyme of the engineered pathway may be under the control of a second promoter, wherein the first and the second promoter have different strengths. For example, the first promoter may be stronger than the second promoter or the second promoter may be stronger than the first promoter. Consequently, the level of a first enzyme may be increased relative to the level of a second enzyme in the engineered pathway by increasing the number of copies of the first enzyme and/or by increasing the promoter strength to which the first enzyme is operably linked to relative to the promoter strength to which the second enzyme is operably linked to. In some other embodiments, the plurality of enzymes of the engineered pathway may be under the control of the same promoter. In other embodiments, altering the ribosomal binding site affects relative translation and expression of different enzymes in the pathway. Altering the ribosomal binding site can be used alone to control relative expression of enzymes in the pathway, or it can be used in concert with the aforementioned promoter modifications and codon optimization that also affects gene expression levels.

In an exemplary embodiment, expression of the potential pathway enzymes may be dependent upon the presence of a substrate that the pathway enzyme will act on in the reaction mixture. For example, expression of an enzyme that catalyzes conversion of A to B may be induced in the presence of A in the media. Expression of such pathway enzymes may be induced either by adding the compound that causes induction or by the natural build-up of the compound during the process of the biosynthetic pathway (e.g., the inducer may be an intermediate produced during the biosynthetic process to yield a desired product).

One of ordinary skill in the art should appreciate that the list of the enzymes provided in the tables is based upon the chemical reaction shown in the figures and that the enzymes are chosen based upon their ability, or potential engineered ability, to catalyze the reaction shown in, for example, FIG. 2. It is possible for a single enzyme to catalyze two reactions that are chemically similar but are assigned to different pathways. This is because some enzymes can accept more than one reactant. In some instances, the enzyme may be associated with different enzyme classification numbers (e.g. EC numbers). In some instances, enzymes have not been assigned an EC number. In these exceptional cases a literature reference is provided.

In some embodiments, computer-implemented design techniques may be used to generate alternative pathways for generating an organic compound of interest. In some embodiments, the databases contain genomic information and their link may be utilized for designing novel metabolic pathways. Examples of databases are MetaCyc (a database of metabolic pathways and enzymes), the University of Minnesota biocatalysis/biodegradation database (a database of microbial catalytic reactions and biodegradation pathways for organic chemical compounds), LGAND (a composite database that provides information about metabolites and other chemical compounds, substrate-product relations representing metabolic and other reactions and information about enzyme molecules) and KEGG (Kyoto Encyclopedia of Genes and Genomes). Specific polypeptide sequences that are relevant for the pathways described herein are available using the Uniport number as provided by the Universal Protein Resource database. A database of pathway components may also contain components of predicted, putative, or unknown functions. It may also contain pseudo-components of defined function that may have an undefined composition. In some embodiments, a program may design combinations of regulatory and/or functional elements that are in the public domain (e.g., that are not covered by patent rights and/or are not subject to a licensing fee). Databases of freely available genetic elements may be generated and/or used as a source of nucleic acid sequences that can be combined to produce alternative pathways. Alternative pathways containing different combinations of known functional and/or regulatory elements (e.g., from different species) may be designed, assembled, and/or tested. Libraries including variations in enzymatic element regions may be used to ascertain the relative effects of different types of enzymes or of different variants of the same enzyme. Libraries including variations in regulatory element regions may be used to ascertain the optimal expression level or regulatory control among a set of genes. In some embodiments, the functional properties of different engineered pathways may be tested in vivo by transforming host cells or organisms with the appropriate assembled nucleic acids, and assaying the properties of the engineered organisms. In some embodiments, the functional properties of different engineered pathways may be tested in vitro by isolating components expressed from assembled nucleic acids and testing the appropriate combinations of components in an in vitro system.

Aspects of the invention provide several metabolic pathways that can be used to produce organic compounds such as the Products described herein. Moreover, the Products can be converted in vitro through enzymatic or chemical reactions into additional molecules of interest. These pathways are shown in FIG. 2. Accordingly, aspects of the invention provide a recombinant microorganism having an engineered biosynthetic pathway shown in FIG. 2. These engineered microorganisms may be also genetically engineered to increase succinate production and divert succinate to 4-hydroxybutyryl-CoA (FIG. 1). Accordingly, in some embodiments, recombinant microorganisms have at least one gene for enhanced succinate production that is expressed at a level lower or higher than that expressed prior to manipulation of the microorganism or in a comparable microorganism which has not been manipulated. Genes are selected from the group of genes which play a key role in the biosynthesis of succinate such as those described EP2220232. The up regulation of succinate production and/or 4-hydroxybutyryl-CoA through one or more of the genetic manipulations can be used in combination with one or more enzymes selected from anyone of Tables 1-9 to produce Products.

As described in FIG. 2, acetyl-CoA and 4-hydroxybutyryl CoA can be converted to 6-hydroxy-b-ketohexanoyl-CoA (6-hydroxy-3-oxo-hexanoyl-CoA) with an enzyme selected from those described in Table 1, below. One of ordinary skill in the art will appreciate that variants of the enzymes that maintain the desired activity can also be designed and expressed. These variants can be for example enzymes that have been codon optimized, such as those shown in Example 1, or variants that are altered to increase desired Product production.

TABLE 1

Reaction 1, FIG. 2

| Enzyme | E.C. Number | Uniprot |
|---|---|---|
| CoA C-acetyltransferase/thiolase | 2.3.1.X | |
| acetyl-CoA C-acetyltransferase | 2.3.1.9 | G0ETJ1, D8NTD8, F4A727, ref 1 |

TABLE 1-continued

Reaction 1, FIG. 2

| Enzyme | E.C. Number | Uniprot |
|---|---|---|
| 3-oxoadipyl-CoA thiolase | 2.3.1.174 | Q8VPF1, P0C7L2, Q43935 |
| 3-oxo-5,6-dehydrosuberyl-CoA thiolase | 2.3.1.223 | P0C7L2 |

Ref 1, Stim-Herndon KP, Petersen DJ, Bennett GN. Characterization of an acetyl-CoA C-acetyltransferase (thiolase) gene from Clostridium acetobutylicum ATCC 824. Gene. 1995 Feb 27;154(1):81-5. PubMed PMID: 7867955.

As described in FIG. 2, malonyl-CoA and 4-hydroxybutyryl CoA can be converted to 6-hydroxy-3-oxo-hexanoyl-CoA with an enzyme selected from those described in Table 1, below. One of ordinary skill in the art will appreciate that variants of the enzymes that maintain the desired activity can also be designed and expressed. These variants can be for example enzymes that have been codon optimized, such as those shown in Example 1, or variants that are altered to increase desired Product production.

TABLE 2

Reaction 2, FIG. 2

| Enzyme | E.C. Number | Uniprot |
|---|---|---|
| CoA synthase-decarboxylase/thiolase | 2.3.1.X | |
| 6-methylsalicylic-acid synthase | 2.3.1.165 | P22367 |
| acetoacetyl-CoA synthase | 2.3.1.194 | D7URV0 |
| 3-oxoacyl-CoA synthase | 2.3.1.199 | P39540 |
| tables | 2.3.1.206 | B1Q2B6 |
| noranthrone synthase | 2.3.1.221 | No Uniprot |

As described in FIG. 2, malonyl-ACP and 4-hydroxybutyryl CoA can be converted to 6-hydroxy-3-oxo-hexanoyl-CoA with an enzyme selected from those described in Table 1, below. One of ordinary skill in the art will appreciate that variants of the enzymes that maintain the desired activity can also be designed and expressed. These variants can be for example enzymes that have been codon optimized, such as those shown in Example 1, or variants that are altered to increase desired Product production.

TABLE 3

Reaction 3, FIG. 3

| Enzyme | E.C. Number | Uniprot |
|---|---|---|
| ACP synthase-decarboxylase/thiolase | 2.3.1.X | |
| beta-ketoacyl-[acyl-carrier-protein] synthase I | 2.3.1.41 | P99159 |
| beta-ketoacyl-[acyl-carrier-protein] synthase II | 2.3.1.179 | P0AAI5 |
| beta-ketoacyl-[acyl-carrier-protein] synthase III | 2.3.1.180 | O07600 |

6-hydroxy-3-oxohexanoyl CoA can be reacted with one or more enzymes selected from those shown in Table 4, below to form 3,6-dihydroxy-hexanoyl-CoA.

TABLE 4

Reaction 4, FIG. 2

| Enzyme | E.C. Number | Uniprot |
| --- | --- | --- |
| 3-oxo-CoA dehydrogenase | 1.1.1.X | |
| 3-hydroxyadipoyl-CoA dehydrogenase | 1.1.1.35 | B0VBA5, Q99714, ref1 |
| 3-hydroxybutyryl-CoA dehydrogenase | 1.1.1.157 | P52041, O53753 |
| 3-hydroxy-2-methylbutyryl-CoA dehydrogenase | 1.1.1.178 | O70351, E4R870 |
| long-chain-3-hydroxyacyl-CoA dehydrogenase | 1.1.1.211 | Q88L88, Q64428 |
| 3-hydroxypimeloyl-CoA dehydrogenase | 1.1.1.259 | ref2 |
| very-long-chain 3-oxoacyl-CoA reductase | 1.1.1.330 | P38286, Q0VH86 |

Ref1 Parke D, Garcia M A, Ornston L N. *Cloning and genetic characterization of dca genes required for beta-oxidation of straight-chain dicarboxylic acids in Acinetobacter sp. strain ADP*1. Appl Environ Microbiol. 2001 October; 67(10):4817-27

Ref2—Harrison F H, Harwood C S. *The pimFABCDE operon from Rhodopseudomonas palustris mediates dicarboxylic acid degradation and participates in anaerobic benzoate degradation.* Microbiology. 2005 March; 151(Pt 3):727-36

3,6,-dihydroxy-hexanoyl-CoA can be reacted with one or more enzymes selected from those shown in Table 5, below to form 6-hydroxy-2-hexenoyl-CoA.

TABLE 5

Reaction 5, FIG. 2

| Enzyme | E.C. Number | Uniprot |
| --- | --- | --- |
| enolyl-CoA dehydratase | 4.2.1.X | |
| enoyl-CoA hydratase | 4.2.1.17 | P76082, P14604 |
| methylglutaconyl-CoA hydratase | 4.2.1.18 | Q3HW12, Q13825 |
| 3-Hydroxybutyryl-CoA dehydratase | 4.2.1.55 | P52046, Q65LU4 |
| Isohexenylglutaconyl-CoA hydratase | 4.2.1.57 | Q4K8Z3 |
| 3-hydroxyacyl-[acyl-carrier-protein] dehydratase | 4.2.1.59 | P0A6Q3 |
| long-chain-enoyl-CoA hydratase | 4.2.1.74 | |
| 3-hydroxypropionyl-CoA dehydratase | 4.2.1.116 | A4YI89 |
| enoyl-CoA hydratase 2 | 4.2.1.119 | Q8VYI3, P97852 |
| 4.2.1.134 | 4.2.1.134 | Q8VZB2 |

6-hydroxy-2-hexenoyl-CoA can be reacted with one or more enzymes selected from those shown in Table 6, below to 6-hydroxyhexanoyl-CoA.

TABLE 6

Reaction 6, FIG. 2

| Enzyme | E.C. Number | Uniprot |
| --- | --- | --- |
| acrylyl-CoA reductase | 1.3.1.X | |
| acyl-CoA dehydrogenase | 1.3.8.X | |
| acrylyl-CoA reductase | 1.3.1.B1 | |
| acyl-CoA dehydrogenase | 1.3.1.8 | Q3IAA0 |
| enoyl-[acyl-carrier-protein] reductase | 1.3.1.9 | P54616 |
| enoyl-[acyl-carrier-protein] reductase (NADPH, B-specific) | 1.3.1.10 | Q8WZM3 |
| cis-2-enoyl-CoA reductase | 1.3.1.37 | |
| trans-2-enoyl-CoA reductase | 1.3.1.38 | Q9BY49 |

TABLE 6-continued

Reaction 6, FIG. 2

| Enzyme | E.C. Number | Uniprot |
| --- | --- | --- |
| 2-hydroxy-6-oxo-6-phenylhexa-2,4-dienoate reductase | 1.3.1.39 | |
| 2'-hydroxyisoflavone reductase | 1.3.1.45 | P52575 |
| pimeloyl-CoA dehydrogenase | 1.3.1.62 | D3RZ02, D3RZ15, Q0K4A3, Q0K4A2 |
| short-chain acyl-CoA dehydrogenase | 1.3.8.1 | Q06319 |
| medium-chain acyl-CoA dehydrogenase | 1.3.8.7 | P08503 |

6-hydroxyhexanoyl-CoA can be reacted with one or more enzymes selected from those shown in Table 7 to produce 6-hydroxycaproic acid.

TABLE 7

Reactions 7, FIG. 2

| Enzyme | E.C. Number | Uniprot |
| --- | --- | --- |
| CoA transferases | 2.8.3.X | |
| thioesterase/hydrolase | 3.1.2.X | |
| propionate CoA-transferase | 2.8.3.1 | Q9L3F7 |
| glutaconate CoA transferase | 2.8.3.12 | Q59111, ref1 |
| 5-hydroxypentanoate CoA-transferase | 2.8.3.14 | |
| succinyl-CoA hydrolase | 3.1.2.3 | ref 2 |
| 3-hydroxyisobutyryl-CoA hydrolase | 3.1.2.4 | Q6NVY1 |
| acyl-CoA hydrolase | 3.1.2.20 | P44886 |
| 4-hydroxybenzoyl-CoA thioesterase | 3.1.2.23 | P56653 |
| dehydrogenase | 1.1.1.X | |
| long-chain-alcohol dehydrogenase | 1.1.1.192 | A4IP64, A4ISB9, Q9RAG9 | ref1-Substrate Specificity of 2-Hydroxyglutaryl-CoA Dehydratase from Clostridium symbiosum: Toward a Bio-Based Production of Adipic Acid Anutthaman Parthasarathy, Antonio J Pierik, Jörg Kahnt, Oskar Zelder, and Wolfgang Buckel Biochemistry 2011 50 (17), 3540-3550"
ref 2 1: Westin MA, Hunt MC, Alexson SE. The identification of a succinyl-CoA thioesterase suggests a novel pathway for succinate production in peroxisomes. J Biol Chem. 2005 Nov 18;280(46):38125-32. Epub 2005 Aug 31. PubMed PMID: 16141203.

6-hydroxycaproic acid can then be converted to adipate semialdehyde using one or more of the enzymes listed in Table 8, below.

TABLE 8

Reaction 8, FIG. 2

| Enzyme | E.C. Number | Uniprot |
| --- | --- | --- |
| alcohol dehydrogenase | 1.1.1.X | |
| alcohol dehydrogenase | 1.1.1.1 | F9VMI9, Q76HN6, Q9QYY9 |
| alcohol dehydrogenase | 1.1.1.2 | C1IWT4, C6GFB1 |
| aldehyde reductase | 1.1.1.21 | O60218 |
| glycerol dehydrogenase (NADP+) | 1.1.1.72 | Q5FQJ0 |
| octanol dehydrogenase | 1.1.1.73 | P46415 |
| cyclohexanol dehydrogenase | 1.1.1.245 | ref1 |
| 6-hydroxyhexanoate dehydrogenase | 1.1.1.258 | M1LWP7, ref2 |
| long-chain-alcohol dehydrogenase | 1.1.1.192 | A4IP64, A4ISB9, Q9RAG9 | ref1 Enzyme reactions involved in anaerobic cyclohexanol metabolism by a denitrifting *Pseudomonas* species Dangel, W.; Tschech, A.; Fuchs, G.; Arch. Microbiol. 152, 273-279 (1989)
ref2-Donoghue NA, Trudgill PW. The metabolism of cyclohexanol by Acinetobacter NCIB 9871. Eur J Biochem, 1975 Dec 1;60(1):1-7. PubMed PMID; 1261.

Adipate semialdehyde can then be converted to 6-aminocaproic acid using on or more of the enzymes shown in Table 9, below.

TABLE 9

Reaction 9, FIG. 2

| Enzyme | E.C. Number | Uniprot |
| --- | --- | --- |
| transaminase | 2.6.1.X | |
| beta-alanine-pyruvate transaminase | 2.6.1.18 | Q3KIH7, P28269, |
| 4-aminobutyrate-2-oxoglutarate transaminase | 2.6.1.19 | P80147, G8PZ77, 4KKA1 |
| 4-aminobutyrate-2-oxoglutarate transaminase | 2.6.1.13 | P38021 |
| (S)-3-amino-2-methylpropionate transaminase | 2.6.1.22 | P80147 |
| L-lysine 6-transaminase | 2.6.1.36 | Q5XPV2 |
| lysine-pyruvate 6-transaminase | 2.6.1.71 | ref 1 |
| diaminobutyrate-2-oxoglutarate transaminase | 2.6.1.76 | P56744 |
| 4-aminobutyrate-pyruvate transaminase | 2.6.1.96 | Q94CE5 |

Ref 1-Schmidt, H.; Bode, R.; Birnbaum, D. A novel enzyme, L-lysine:pyruvate aminotransferase, catalyses the first step of lysine catabolism in *Pichia guilliermondii*. FEMS Microbiol. Lett. 49, 203-206 (1988)

One of ordinary skill in the art will appreciate that FIG. 2 shows a variety of different pathways that can be used to form Products. Accordingly, a variety of recombinant microorgansims are described which are engineered to include one or more enzymes show in FIG. 2 and the accompanying tables, in combination with one or more recombinant sequences to up regulate succinate and/or 4-hydrobutyryl-CoA production. Other recombinant microorganisms include recombinant sequences that allow for the expression of two, three, four or more enzymes described in FIG. 2 and the accompanying text. The following exemplary microorgansims can be used to produce Products.

B. Making Products

The recombinant microorganisms described herein may be cultivated continuously or discontinuously in a batch process (batch cultivation) or in a fed-batch process (feed process) or repeated fed-batch process (repetitive feed process) for the purposes of producing products.

The culture medium to be used must satisfy in a suitable manner the requirements of the respective strains. Descriptions of culture media for various microorganisms are contained in the handbook "Manual of Methods for General Bacteriology" of the American Society for Bacteriology (Washington D.C., USA, 1981). Media must contain suitable carbon sources such as monosaccharides (e.g. glucose and fructose), oligosaccharides (e.g. sucrose, lactose), polysaccharides (e.g. starch and cellulose), oils and fats or mixture thereof. Media must contain a nitrogen source such as organic nitrogen-containing compounds such as peptones, yeast extract, meat extract, malt extract, corn steep liquor, soy bean flour and urea, or inorganic compounds such as ammonium sulfate, ammonium chloride, ammonium phosphate, ammonium carbonate and ammonium nitrate. The nitrogen sources may be used individually or as a mixture.

In addition to the carbon sources and nitrogen sources, media must contain suitable minerals, salts, cofactors, buffers and other components, known to those skilled in the art, suitable for growth of the culture and promotion of product production.

Typically cells are grown at a temperature in the range of 20° C. to about 45° C. and preferably 25° C. to 40° C. in an appropriate medium. Suitable growth media includes common commercially available media such as Luria Bertani (LB) broth, Yeast medium (YM) or any synthetic or defined media. Suitable pH ranges are between pH 5.0 to pH 9.0, in some cases suitable pH ranges may fall below pH 5, such as to between pH 3-5 when acidiphilic organisms are used. In order to regulate the pH of the culture, basic compounds such as sodium hydroxide, potassium hydroxide, ammonia or ammonia water, or acidic compounds such as phosphoric acid or sulfuric acid are used as appropriate. Culture may be performed under aerobic or anaerobic conditions.

In accordance with the methods described herein, reaction mixtures for pathway development may be carried out in any vessel that permits cell growth and/or incubation. For example, a reaction mixture may be a bioreactor, a cell culture flask or plate, a multiwell plate (e.g., a 96, 384, 1056 well microtiter plates, etc.), a culture flask, a fermentor, or other vessel for cell growth or incubation.

Screening for the expression of a particular recombinant sequence can be accomplished using any technique known in the art. For example, screening may be carried out by detection of expression of a selectable marker, which, in some genetic circumstances, allows cells expressing the marker to survive while other cells die (or vice versa). Efficient screening techniques are needed to provide efficient development of novel pathways using the methods described herein. Preferably, suitable screening techniques for compounds produced by the enzymatic pathways allow for a rapid and sensitive screen for the properties of interest. Visual (colorimetric) assays are optimal in this regard, and are easily applied for compounds with suitable light absorption properties. More sophisticated screening technologies include, for instance, high-throughput HPLC-MS analysis, SPME (Solid Phase Microextraction) and GC-MS (Gas chromatography-mass spectrometry) (see Handbook of analytical derivatization reaction, D. R. Knapp; John Wiley & Sons, 1979). In some instance, screening robots are connected to HPLC-MS systems for automated injection and rapid sample analysis. These techniques allow for high-throughput detection and quantification of virtually any desired compound.

Produced products of interest may be isolated from the fermentation medium or cell extract using methods known in the art. For example, solids or cell debris may be removed by centrifugation, filtration, decantation and the like. Products may be isolated by distillation, liquid-liquid extraction, membrane evaporation, adsorption, or using any methods known in the art.

In some embodiments, identification of the product of interest may be performed using an HPLC. For example, the standard samples are prepared with known amounts of the organic product in the medium (e.g. HMDA and ACA). The retention time of the adipic acid produced can then be compared to that of the authentic standard. In some embodiments, identification of the product of interest may be performed using a GC-MS. The resolved samples are then analyzed by a mass selective detector and compared to previous mass spectra and retention time of authentic standards.

The practice of the present methods will employ, unless otherwise indicated, conventional techniques of cell biology, cell culture, molecular biology, transgenic biology, microbiology, recombinant DNA, and immunology, engineering, robotics, optics, computer software and integration. The techniques and procedures are generally performed according to conventional methods in the art and various general references. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames &

S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986); Lakowicz, J. R. Principles of Fluorescence Spectroscopy, New York:Plenum Press (1983), and Lakowicz, J. R. Emerging Applications of Fluorescence Spectroscopy to Cellular Imaging: Lifetime Imaging, Metal-ligand Probes, Multi-photon Excitation and Light Quenching, Scanning Microsc. Suppl. VOL. 10 (1996) pages 213-24, for fluorescent techniques, Optics Guide 5 Melles Griot® Irvine Calif. for general optical methods, Optical Waveguide Theory, Snyder & Love, published by Chapman & Hall, and Fiber Optics Devices and Systems by Peter Cheo, published by Prentice-Hall for fiber optic theory and materials.

EXAMPLES

The following reference materials are used in the following Examples: Recombinant DNA manipulations generally follow methods described by Sambrook et al. Molecular Cloning: A Laboratory Manual, Third Edition, Sambrook and Russell, 2001, Cold Spring Harbor Laboratory Press, 3rd Edition. Restriction enzymes are purchased from New England Biolabs (NEB). T4 DNA ligase is obtained from Invitrogen. FAST-LINK™ DNA Ligation Kit is obtained from Epicentre. Zymoclean Gel DNA Recovery Kit and DNA Clean & Concentrator Kit are obtained from Zymo Research Company. Maxi and Midi Plasmid Purification Kits are obtained from Qiagen. Antarctic phosphatase is obtained from NEB. Agarose (electrophoresis grade) is obtained from Invitrogen. TE buffer contains 10 mM Tris-HCl (pH 8.0) and 1 mM Na2EDTA (pH 8.0). TAE buffer contains 40 mM Tris-acetate (pH 8.0) and 2 mM Na2EDTA.

In Examples 1, restriction enzyme digests were performed in buffers provided by NEB. A typical restriction enzyme digest contains 0.8 µg of DNA in 8 µL of TE, 2 µL of restriction enzyme buffer (10× concentration), 1 µL of bovine serum albumin (0.1 mg/mL), 1 µL of restriction enzyme and 8 µL TE. Reactions are incubated at 37° C. for 1 h and analyzed by agarose gel electrophoresis. The DNA used for cloning experiments was digested and the reaction was terminated by heating at 70° C. for 15 min followed by extraction of the DNA using Zymoclean gel DNA recovery kit.

The concentration of DNA in the sample was determined as follows. An aliquot (10 µL) of DNA was diluted to 1 mL in TE and the absorbance at 260 nm was measured relative to the absorbance of TE. The DNA concentration was calculated based on the fact that the absorbance at 260 nm of 50 µg/mL of double stranded DNA is 1.0.

Agarose gel typically contains 0.7% agarose (w/v) in TAE buffer. Ethidium bromide (0.5 µg/ml) is added to the agarose to allow visualization of DNA fragments under a UV lamp. Agarose gel were run in TAE buffer. The size of the DNA fragments was determined using two sets of 1 kb Plus DNA Ladder obtained from Invitrogen.

Example 1

Expression of Thiolase Sequences Useful for Making 6-hydroxy-3-oxo-hexanoyl-CoA

*E coli* optimized thiolase genes were synthesized and cloned into pTrcHisA (Life Technologies (formerly Invitrogen)). The optimized sequences were as follows: SEQ ID NOS 1 and 2 (nucleic acid sequence and amino acid sequence, respectively) show the optimized bktB sequences originally from Cupriavidus necator, strain ATCC 17699, EC NOS 2.3.1.16 and 2.3.9, having a recommended name of Beta-ketothiolase; SEQ ID NOS 3 and 4 (nucleic acid sequence and amino acid sequence, respectively) show the PhaA optimized sequences originally from *Ralstonia* sp., strain EMBL EON20543.1, EC NO 2.3.1.9, having a suggested name of acyltransferase; and SEQ ID NOS 5 and 6 (nucleic acid sequence and amino acid sequence, respectively) show the thl optimized sequences originally from *Clostridium acetobutylicum*, strain ATCC 824, EC 2.3.1.9, suggested name acetyl-CoA acetyltransferase.

Plasmids containing the optimized thiolase genes were transformed into BL21 *E. coli* cells. Empty plasmid pTrcHisA was also transformed as a negative control. For expression and characterization experiments, shake flasks containing 40 mL TB were innoculated at 5% from overnight cultures. Flasks were incubated at 30° C. at 250 rpm shaking for 2 hours, then protein production was induced with 0.2 mM IPTG and incubated for 4 more hours at 30° C. while shaking. Cells were harvested by centrifugation and pellets were stored at −80° C.

Activity of thiolase candidates were assessed with an in vitro assay using DTNB (5,5'-Dithiobis(2-nitrobenzoic acid)) as an indicator. The enzyme activity was tested using two different substrates: crotonoyl-CoA and butyryl-CoA. The DTNB interacts with the free thiol created by the condensation of acetyl-CoA and the substrate present (butyryl-CoA or crotonoyl-CoA). Unless otherwise specified, all chemicals were purchased from Sigma-Aldrich Chemical Company, ST. Louis, Mo.

Cells were lysed using mechanical disruption using a BeadBeater (BioSpec products, Bartlesville, Okla.) using the manufacturer's instructions. The cell lysate was partially clarified by centrifugation (14,000 G for 5 minutes). Protein concentrations of the resulting clarified lysates were measured via BioRad Total Protein assay using the manufacturer's instructions. Lysates were normalized by protein concentration by dilution in 10 mM Tris buffer. The normalized lysates were diluted 1 to 5 in 10 mM Tris buffer. 20 ul of lysate was added to each well for the 96-well plate assay. Each condition was performed in triplicate.

The reaction mixture contains 10 mM Tris pH 7.4, 5 mM MgSO4, 0.2 mM acetyl-coA, 0.5 mM DTNB, 0.5 mM substrate (either butyryl-CoA or crotonoyl-CoA). The pH of each reaction mixture was adjusted to approximately pH 7.4. To start the reaction, 180 ul of reaction mix was added to the each well already containing 20 ul lysate. The reactions in these microplates were monitored at 412 nm. Readings were taken every 9 seconds for 5 minutes and the data was used to calculate activities of each enzyme. The reactions using crotonoyl-CoA as substrate required a 60 sec incubation period before rates were able to be measured.

Figure 3A:
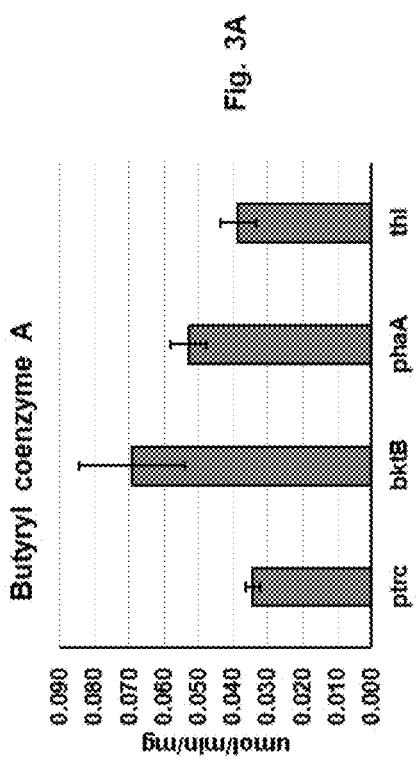
FIGS. 3A and 3B show graphs of data relating to thiolase activity with butyryl-CoA as compared to cells containing an empty vector, and thiolase activity with crotonyl coenzyme A as compared to cells containing an empty vector, respectively.
Figure 3B:
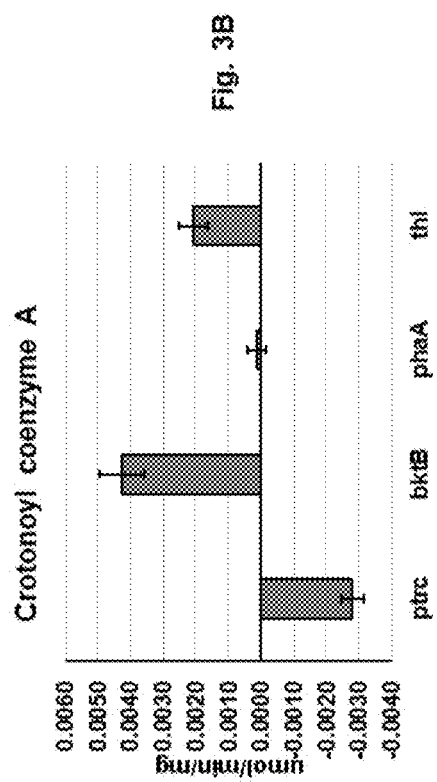

Results are shown in FIG. 3. Thiolase activity was observed with butyryl-CoA as a substrate as compared to cells containing empty vector (FIG. 3A). Thiolase activity was observed with crotonyl-CoA as a substrate as compared to cells containing empty vector (FIG. 3B). Background absorbances as measured by same reaction with no substrate present were subtracted. An incubation period of 60 seconds for equilibrium of crotonyl-CoA reactions was required before measurement of activity began. Errors bars in the graphs reflect the standard deviations calculated for the averages for each condition performed in triplicate.

TABLE 10

Table of activity of thiolases with different substrates with background (no substrate) subtracted

| | Average Activity with background subtracted (umol/min/mg) | | Stdev | |
|---|---|---|---|---|
| | Butyryl coenzyme A | Crotonoyl coenzyme A | Butyryl coenzyme A | Crotonoyl coenzyme A |
| ptrc empty vector control | 0.034 | −0.0028 | 0.0022 | 0.00035 |
| bktB | 0.069 | 0.0043 | 0.0152 | 0.00069 |
| phaA | 0.053 | 0.0001 | 0.0053 | 0.00027 |
| thl | 0.039 | 0.0021 | 0.0052 | 0.00045 |

Example 2

Cloning of a Plasmid Expressing Enzymatic Pathways for Making Aminocaproic Acid

The DNA fragments encoding CoA synthase-decarboxylase/thiolase (Step 1 in FIG. 2), 3-oxo-CoA dehydrogenase (Step 4 in FIG. 2), enolyl-CoA dehydrase (Step 5 in FIG. 2), acrylyl-CoA reductase (Step 6 in FIG. 2), CoA transferases (Step 7 in FIG. 2), alcohol dehydrogenase (Step 8 in FIG. 2) and aminotransferase (Step 9, FIG. 2) are cloned into an expression vector. Gene candidates and their sequence are shown in Tables 1, 4, 5, 6, 7, 8, and 9. The resulting plasmid that successfully transcribes all pathway genes is designated pBA901.

Example 3

Transformation of *E. coli* with Plasmid Containing Nucleic Acid Sequence Encoding Pathway Enzymes Plasmid DNA molecules of pBA901 are introduced into target *E. coli* cells engineered with the referenced pathway described in Example 2, above by chemical transformation or electroporation. For chemical transformation, cells are grown to mid-log growth phase, as determined by the optical density at 600 nm (0.5-0.8). The cells are harvested, washed and finally treated with $CaCl_2$. To chemically transform these *E. coli* cells, purified plasmid DNA is allowed to mix with the cell suspension in a microcentrifuge tube on ice. A heat shock is applied to the mixture and followed by a 30-60 min recovery incubation in rich culture medium. For electroporation, *E. coli* cells grown to mid-log growth phase are washed with water several times and finally resuspended into 10% glycerol solution. To electroporate DNA into these cells, a mixture of cells and DNA is pipetted into a disposable plastic cuvette containing electrodes. A short electric pulse is then applied to the cells which forms small holes in the membrane where DNA can enter. The cell suspension is then incubated with rich liquid medium followed by plating on solid agar plates. Detailed protocol can be obtained in Molecular Cloning: A Laboratory Manual, Third Edition, Sambrook and Russell, 2001, Cold Spring Harbor Laboratory Press, 3rd Edition.

*E. coli* cells of the BL21 strain are transformed with plasmid pBA901. BL21 is a strain of *E. coli* having the genotype: B F- dcm ompT hsdS(rB- mB-) gal λ. BL21 transformant of pBA901 is also called biocatalyst BA901.

Example 4

Culture of Transformed *E. coli*

For the following Examples, Examples 5-6, the Growth Medium is prepared as follows:

All solutions are prepared in distilled, deionized water. LB medium (1 L) contained Bacto tryptone (i.e. enzymatic digest of casein) (10 g), Bacto yeast extract (i.e. water soluble portion of autolyzed yeast cell) (5 g), and NaCl (10 g). LB-glucose medium contained glucose (10 g), $MgSO_4$ (0.12 g), and thiamine hydrochloride (0.001 g) in 1 L of LB medium. LB-freeze buffer contains $K_2HPO_4$ (6.3 g), $KH_2PO_4$ (1.8 g), $MgSO_4$ (1.0 g), $(NH_4)_2SO_4$ (0.9 g), sodium citrate dihydrate (0.5 g) and glycerol (44 mL) in 1 L of LB medium, M9 salts (1 L) contains $Na_2HPO_4$ (6 g), $KH_2PO_4$ (3 g), $NH_4Cl$ (1 g), and NaCl (0.5 g). M9 minimal medium contains D-glucose (10 g), $MgSO_4$ (0.12 g), and thiamine hydrochloride (0.001 g) in 1 L of M9 salts. Antibiotics are added where appropriate to the following final concentrations: ampicillin (Ap), 50 µg/mL; chloramphenicol (Cm), 20 µg/mL; kanamycin (Kan), 50 µg/mL; tetracycline (Tc), 12.5 µg/mL. Stock solutions of antibiotics are prepared in water with the exceptions of chloramphenicol which is prepared in 95% ethanol and tetracycline which is prepared in 50% aqueous ethanol. Aqueous stock solutions of isopropyl-β-D-thiogalactopyranoside (IPTG) are prepared at various concentrations.

The standard fermentation medium (1 L) contains K2HPO4 (7.5 g), ammonium iron (III) citrate (0.3 g), citric acid monohydrate (2.1 g), and concentrated H2SO4 (1.2 mL). Fermentation medium is adjusted to pH 7.0 by addition of concentrated NH4OH before autoclaving. The following supplements are added immediately prior to initiation of the fermentation: D-glucose, MgSO4 (0.24 g), potassium and trace minerals including $(NH_4)6(Mo_7O_{24}) \cdot 4H_2O$ (0.0037 g), $ZnSO_4 \cdot 7H_2O$ (0.0029 g), $H_3BO_3$ (0.0247 g), $CuSO_4 \cdot 5H_2O$ (0.0025 g), and $MnCl_2 \cdot 4H_2O$ (0.0158 g). IPTG stock solution is added as necessary (e.g., when optical density at 600 nm lies between 15-20) to the indicated final concentration. Glucose feed solution and $MgSO_4$ (1 M) solution are autoclaved separately. Glucose feed solution (650 g/L) is prepared by combining 300 g of glucose and 280 mL of $H_2O$. Solutions of trace minerals and IPTG are sterilized through 0.22-µm membranes. Antifoam (Sigma 204) is added to the fermentation broth as needed.

Example 5

Shake Flask Experiments for Aminocaproic Acid Production

Seed inoculant is started by introducing a single colony of biocatalyst BA901 picked from a LB agar plate into 50 mL TB medium (1.2% w/v Bacto Tryptone, 2.4% w/v Bacto Yeast Extract, 0.4% v/v glycerol, 0.017 M $KH_2PO_4$, 0.072 M $K_2HPO_4$). Culture is grown overnight at 37° C. with agitation at 250 rpm until they are turbid. All of the culture conditions include suitable selective pressure to ensure that the plasmid containing the biosynthetic pathway genes is maintained and expressed in the host cell. A 2.5 mL aliquot of this culture is subsequently transferred to 50 mL of fresh TB medium. After culturing at 37° C. and 250 rpm for an additional 3 h, IPTG is added to a final concentration of 0.2 mM. The resulting culture is allowed to grow at 27° C. for 4 hours. Cells are harvested, washed twice with PBS medium, and resuspended in 0.5 original volume of M9 medium supplemented with glucose (2 g/L). The whole cell suspension is then incubated at 27° C. for 48 h. Samples is taken and analyzed by GC/MS and 1H-NMR. Compared to the control BL21 strain transformed with empty plasmids that no aminocaproic acid production is detected, E. coli BA901 produces aminocaproic acid at a concentration above 0.5 g/L in shake flasks from glucose.

Example 6

Cultivation of Aminocaproic Acid Biocatalyst Under Fermentor-Controlled Conditions Fed-batch fermentation is performed in a 2 L working capacity fermentor. Temperature, pH and dissolved oxygen are controlled by PID control loops. Temperature is maintained at 37° C. by temperature adjusted water flow through a jacket surrounding the fermentor vessel at the growth phase, and later adjusted to 27° C. when production phase starts. The pH is maintained at 7.0 by the addition of 5 N KOH and 3 $NH_3PO_4$. Dissolved oxygen (DO) level is maintained at 20% of air saturation by adjusting air feed as well as agitation speed.

Inoculant is started by introducing a single colony of BA901 picked from an LB agar plate into 50 mL TB medium. The culture is grown at 37° C. with agitation at 250 rpm until the medium is turbid. Subsequently a 100 mL seed culture is transferred to fresh M9 glucose medium. After culturing at 37° C. and 250 rpm for an additional 10 h, an aliquot (50 mL) of the inoculant (OD600=6-8) is transferred into the fermentation vessel and the batch fermentation is initiated. The initial glucose concentration in the fermentation medium is about 40 g/L.

Cultivation under fermentor-controlled conditions is divided into two stages. In the first stage, the airflow is kept at 300 ccm and the impeller speed is increased from 100 to 1000 rpm to maintain the DO at 20%. Once the impeller speed reaches its preset maximum at 1000 rpm, the mass flow controller starts to maintain the DO by oxygen supplementation from 0 to 100% of pure 02.

The initial batch of glucose is depleted in about 12 hours and glucose feed (650 g/L) is started to maintain glucose concentration in the vessel at 5-20 g/L. At OD600=20-25, IPTG stock solution is added to the culture medium to a final concentration of 0.2 mM. The temperature setting is decreased from 37 to 27° C. and the production stage (i.e., second stage) is initiated. Production stage fermentation is run for 48 hours and samples are removed to determine the cell density and quantify metabolites.

The aminocaproic acid production is measured by GS/MS and 1H-NMR. Compared to the control BL21 strain transformed with empty plasmids, E. coli BA091 produced aminocaproic acid from glucose at a concentration of above 0.5 g/L under fermentor-controlled conditions.

Although the invention has been described with reference to the examples provided above, it should be understood that various modifications can be made without departing from the spirit of the invention.

The invention claimed is:

1. A recombinant microorganism genetically engineered to produce adipate semialdehyde from 4-hydroxybutyryl-CoA, the recombinant microorganism comprising a first exogenous nucleic acid encoding a CoA synthase of class E.C. 2.3.1.X that catalyzes a substrate to product conversion of malonyl-CoA and 4-hydroxybutyryl-CoA to 6-hydroxy-3-oxo-hexanoyl-CoA and $CO_2$, wherein the recombinant microorganism produces adipate semialdehyde from 4-hydroxybutyryl-CoA via the intermediates: 6-hydroxy-3-oxo-hexanoyl-CoA; 3,6-dihydroxyhexanoyl-CoA; 6-hydroxy-2-hexenoyl-CoA; 6-hydroxyhexanoyl-CoA; and 6-hydroxycaproic acid.

2. The recombinant microorganism of claim 1, wherein the CoA synthase decarboxylase is a CoA synthase decarboxylase of class E.C. 2.3.1.165, E.C. 2.3.1.194, E.C. 2.3.1.199, E.C. 2.3.1.206, or E.C. 2.3.1.221.

3. The recombinant microorganism of claim 1, further comprising at least a second exogenous nucleic acid encoding at least one further enzyme selected from an acetyltransferase (E.C. 2.3.1.X), ACP synthase decarboxylase (E.C. 2.3.1.X), 3-oxoCoA dehydrogenase (1.1.1.X), enolyl-CoA dehydratase (E.C. 4.2.1.X), acrylyl-CoA reductase (E.C. 1.3.1.X), acyl-CoA dehydrogenase (E.C. 1.3.8.X), CoA transferase (E.C. 2.8.3.X), thioesterase (E.C. 3.1.2.X), dehydrogenase (E.C. 1.1.1.X), alcohol dehydrogenase (E.D. 1.1.1.X), and transaminase (E.C. 2.6.1.X).

4. The recombinant microorganism of claim 3, further comprising a third exogenous nucleic acid encoding an enzyme that converts 6-hydroxycaproic acid to adipate semialdehyde.

5. The recombinant microorganism of claim 4, further comprising a fourth exogenous nucleic acid encoding an enzyme that converts adipate semialdehyde to an organic molecule selected from 6-aminocaproic acid, adipatic acid, hexamethylenediamine, and 1,6-hexanediol.

6. The recombinant microorganism of claim 1 wherein the recombinant microorganism is a yeast.

7. The recombinant microorganism of claim 1 wherein the recombinant microorganism is a bacteria.

8. The recombinant microorganism of claim 1 wherein the aqueous solubility of each of the intermediates is greater than 20 mg/mL.

9. The recombinant microorganism of claim 3, wherein the recombinant microorganism comprises exogenous nucleic acids encoding at least three of said further enzymes.

10. A recombinant microorganism genetically engineered to produce adipate semialdehyde from 4-hydroxybutyryl- CoA, the recombinant microorganism comprising a first exogenous nucleic acid encoding an enzyme of class E.C. 2.3.1.165, E.C. 2.3.1.194, E.C. 2.3.1.199, E.C. 2.3.1.206, or E.C. 2.3.1.221 that catalyzes a substrate to product conversion of malonyl-CoA and 4-hydroxybutyryl-CoA to 6-hydroxy-3-oxo-hexanoyl-CoA and $CO_2$, and wherein the recombinant microorganism produces adipate semialdehyde from 4-hydroxybutyryl-CoA via the intermediates: 6-hydroxy-3-oxo-hexanoyl-CoA; 3,6-dihydroxyhexanoyl-CoA; 6-hydroxy-2-hexenoyl-CoA; 6-hydroxyhexanoyl-CoA; and 6-hydroxycaproic acid.

11. The recombinant microorganism of claim 10 further comprising a second exogenous nucleic acid encoding an enzyme of class E.C. 2.3.1.9, E.C. 2.3.1.174, or E.C. 2.3.1.223 that catalyzes a substrate to product conversion of acetyl-CoA and 4-hydroxybutyryl-CoA to 6-hydroxy-3-oxo-hexanoyl-CoA, and/or a third exogenous nucleic acid encoding an enzyme of class E.C. 2.3.1.41, E.C. 2.3.1.179, or E.C. 2.3.1.180 that catalyzes a substrate to product conversion of malonyl-ACP and 4-hydroxybutyryl-CoA to 6-hydroxy-3-oxo-hexanoyl-CoA and $CO_2$.

* * * * *